United States Patent [19]

Weaver et al.

[11] Patent Number: 5,283,175
[45] Date of Patent: Feb. 1, 1994

[54] **GENUS-SPECIFIC OLIGOMERS OF *BORRELIA* AND METHODS OF USING SAME**

[75] Inventors: Terry L. Weaver, Fredonia, N.Y.; Darla J. Wise, Blacksburg, Va.

[73] Assignee: The Research Foundation of State University of New York, Albany, N.Y.

[21] Appl. No.: 685,722

[22] Filed: Apr. 15, 1991

[51] Int. Cl.$^5$ .................. C12Q 1/68; C12P 19/34; C07H 17/00; C07H 5/04
[52] U.S. Cl. .................. 435/6; 536/18.4; 536/28.6; 536/24.3; 536/24.33; 925/70; 925/72; 925/77
[58] Field of Search .................. 435/6; 536/27

[56] References Cited

U.S. PATENT DOCUMENTS

| | | |
|---|---|---|
| 4,683,195 | 7/1987 | Mullis et al. |
| 4,683,202 | 7/1987 | Mullis |
| 4,800,159 | 1/1989 | Mullis et al. |
| 4,888,276 | 12/1989 | Shelburne .................. 435/7 |
| 4,965,188 | 10/1990 | Mullis et al. |

FOREIGN PATENT DOCUMENTS

WO8912063 12/1989 PCT Int'l Appl.
WO9002821 3/1990 PCT Int'l Appl.

OTHER PUBLICATIONS

D. Dodge and T. J. White, Abstract D-137, Abstracts of 90th Annual Meeting of the American Society for Microbiology, p. 103 (1990).
D. C. Malloy et al., Abstract D-138, Abstracts of 90th Annual Meeting of the American Society for Microbiology, p. 103 (1990).
D. Wise and T. Weaver, Abstract D-139, Abstracts of 90th Annual Meeting of the American Society for Microbiology, p. 103 (1990).
S. L. Nielsen et al., Molecular and Cellular Probes 4: 73–79 (1990).
D. H. Persing et al., J. Clin. Micro. 28: 566–572 (1990).
Schwan et al. J. Clin Microb. 27(8):1734 (1989).
Goodman et al. Clin. Res. 37(2):429A (1989).
Gassmann et al. Nuc. Acid Res. 17(9):3590 (1989).
Rosa et al. J. Inf. disease 160(6) 1018 (1989).
Malloy et al. J. Clin. Microb. 28(6):1089 (1990).
Schwan & Barbour in "Lyme disease and Related Disorders", Ann. N.Y. Acad. Sc. 539:419 (1988).
Barbour, A., Ann. Int. Med. 110(7) 501 (1989).
Chen et al. FEMS Microb Lett. 57:19 (1989).
Persing et al. Science 249:1420–1423 (1990).
Wallich et al., Infec. & Immun. 58(6):1711–1719 (1990).

*Primary Examiner*—Robert A. Wax
*Assistant Examiner*—Miguel H. Escallon
*Attorney, Agent, or Firm*—Heslin & Rothenberg

[57] ABSTRACT

The subject invention provides DNA oligomers complementary to portions of the flagellin gene of *Borrelia burgdorferi* which can be used to detect the organism, as well as other *Borrelia* species, in a sample. PCR technology can be used to amplify the portion of the flagellin gene which is then detected using a biotinylated probe provided by the subject invention.

16 Claims, 4 Drawing Sheets

GENUS-SPECIFIC OLIGOMERS OF *BORRELIA* AND METHODS OF USING SAME

BACKGROUND OF THE INVENTION

1. Technical Field

This invention relates to enzymatic amplification of DNA encoding a portion of a flagellin gene sequence in *Borrelia*, the portion being conserved among *Borrelia* species. More particularly, the invention relates to DNA oligomers complementary to portions of the flagellin gene of *Borrelia burgdorferi* which can be used to detect the organism, as well as other *Borrelia* species, in a sample.

2. Description of the Prior Art

Throughout this application various publications are referenced by arabic numerals within parentheses. Full citations for these references may be found at the end of the specification immediately preceding the Sequence Listing. The disclosures of these publications in their entireties are hereby incorporated by reference in this application in order to more fully describe the state of the art to which the invention pertains.

Lyme disease is a multisystem disorder caused by the spirochete *Borrelia burgdorferi* (8, 32). The symptoms associated with the early stages of Lyme disease are rather general (eg. fever, malaise, etc.) and make diagnosis difficult (32). Furthermore, the immune response early in Lyme disease is unpredictable which renders antibody detection via ELISA methods of limited diagnostic value (10, 13). However, early detection and treatment reduces the probability of the more severe complications associated with later stages of Lyme disease (31).

One approach to the direct detection of microorganisms that is independent of host immune response is the relatively new technique known as the polymerase chain reaction or PCR (22). [See U.S. Pat. No. 4,683,195, issued Jul. 28, 1987; U.S. Pat. No. 4,683,202, issued Jul. 28, 1987; U.S. Pat. No. 4,800,159, issued Jan. 25, 1989; and U.S. Pat. No. 4,965,188, issued Oct. 23, 1990, each assigned to the Cetus Corporation, for a description of PCR technology. The contents of each of these patents are hereby incorporated by reference.] PCR involves the use of DNA sequence specific primers, a heat-stable DNA polymerase, and repeated temperature cycles of melting, hybridizing, and chain elongation to amplify specific gene sequences a millionfold in several hours. These amplified sequences can be detected in agarose gels or by using specific gene probes (27). Due to the degree of amplification achieved after PCR, detection of a single cell is possible under optimal conditions (23). Because of its sensitivity and specificity, the use of PCR has recently attracted much interest as a potential genetic approach to microbial diagnostics (1, 11, 20, 33).

Rosa and Schwan were the first to apply PCR to the detection of *B. burgdorferi* (26). Purified *B. burgdorferi* DNA was partially digested with a restriction endonuclease. The resultant restriction fragments were then inserted into plasmids and transformed into *Escherichia coli*. Competent clones were then screened, using hybridization techniques, as being "unique" to *B. burgdorferi* as tested against the closely related *B. hermsii*. The *B. burgdorferi* insert for a clone of interest was sequenced. Based upon this sequence, specific oligonucleotide primers were constructed for use in PCR. PCR with these primers was then performed on DNA from 18 strains of *B. burgdorferi*, *B. hermsii*, *B. coriaceae*, *B. parkeri*, *B. turicatae*. *B. anserina*, and *B. crocidurae*. Using this method, 17 of the 18 strains of *B. burgdorferi* were detected; no reactivity was associated with the other Borrelia species tested. Sensitivity to as few as five cells was reported with this assay.

Recently, the target for PCR amplification associated with detection of *B. burgdorferi* has been the outer surface protein (OSP) A gene (24, 25). This gene is located on a linear plasmid associated with the spirochete (4). In a study by Nielsen et al (24), oligonucleotide primers were constructed to the OSP A gene of the prototype strain *B. burgdorferi* B31 (ATCC-35210). Purified *B. burgdorferi* DNA was serially diluted and the number of cells estimated based upon the size of the *B. burgdorferi* genome. PCR was then conducted on the dilutions of *B. burgdorferi* DNA, *B. hermsii*, *Treponema pallidum*, *T. denticola*, *Leptospira interrogans*, and *Staphylococcus aureus*. Products were then identified specifically using a radioactively labeled oligonucleotide probe selected from the OSP A gene region between the two oligonucleotide primers. The assay was able to identify the *B. burgdorferi* DNA to a sensitivity of approximately fifty cells with the aid of hybridization. This assay did not identify any of the other organisms tested.

It has been reported in different studies that European and American strains differ in many ways, such as DNA homology, outer surface proteins, and plasmid composition (3, 6, 7, 17, 21, 29). In addition, it has been reported that European strains are more diverse than American strains (6). In other PCR-based assays for the detection of *B. burgdorferi*, some "unusual" strains were unable to be detected (25, 26). Therefore, one advantage of the subject invention is that it may offer versatility for the detection of many strains of *B. burgdorferi*.

There exists a continual need for efficient and sensitive ways to detect *Borrelia burgdorferi* in order to diagnose Lyme disease. The subject invention therefore provides for the use of PCR for the direct detection of *B. burgdorferi*. Furthermore, the subject invention provides a sensitive nonradioisotopic detection system coupled with PCR, by utilizing a biotinylated probe. The use of biotin as a label is disclosed in PCT International Application Publication No. WO 89/12063, published Dec. 14, 1989 (Mitchell and Merril), the contents of which is hereby incorporated by reference into this application.

SUMMARY OF THE INVENTION

The immune response in early Lyme disease to *Borrelia burgdorferi* antigens is often unpredictable. As an alternative to immunological testing, the polymerase chain reaction (PCR) was used as a means of direct, sensitive detection of the spirochete in vitro. The target for PCR amplification was a 419 bp region of the flagellin gene sequence. After thirty cycles of PCR, the resulting PCR amplification products were immobilized on nitrocellulose membranes and probed using a biotinylated oligonucleotide probe specific for the 419 bp amplification product. Using this method, sensitivity to as few as one to ten spirochetes was observed, suggesting detection approaching the single cell limit. The 419 bp flagellin gene fragment was conserved in both the American and European strains of *B. burgdorferi* and among the *Borrelia* species pathogenic in mammals. No amplification resulted with either *B. anserina* or *Treponema pallidum*. The use of a genus specific probe allows for versatility in detection of mammalian associated borreliae. This versatility also allows for the detection of both American and European strains of *B. burgdorferi* associated with Lyme disease.

It is thus an object of the subject invention to provide DNA oligomers complementary to DNA encoding a portion of a flagellin gene sequence in *Borrelia* which is conserved among *Borrelia* species. This allows genus-specific detection of *Borrelia*.

It is a further object of the subject invention to provide DNA oligomers useful as primers for PCR amplification of the conserved portion of the flagellin gene of *Borrelia*.

It is a still further object of the subject invention to provide a method for detecting the presence of *Borrelia* in a sample using the oligomers of the subject invention. The invention also provides the oligomers in the form of a kit for use in qualitatively and quantitatively detecting *Borrelia* in a sample.

BRIEF DESCRIPTION OF THE FIGURES

These and other objects, advantages and features of the present invention will be more fully understood from the following detailed description of certain embodiments thereof when considered in conjunction with the accompanying drawings in which.

DETAILED DESCRIPTION OF THE INVENTION

The subject invention provides a DNA oligomer comprising a DNA sequence complementary to DNA encoding a portion of a flagellin gene sequence in Borrelia. The size of the portion was determined in order to be easy to work with when the portion is amplified using PCR technology. In one preferred embodiment, the size of the portion is about 400–500 base pairs. A portion of the flagellin gene sequence in *Borrelia burgdorferi* was chosen due to its conservation among *Borrelia* species.

In order to amplify the chosen portion of the flagellin gene sequence, PCR primers were also determined. These primers were chosen based on their G+C content of approximately 50%, as this characteristic is best for hybridization, and based on the lack of internal homology between the primer sequences. The lack of internal homology prevents the primers from hybridizing to themselves, which would decrease the sensitivity of any assay. The two primers chosen were complementary to nucleotide numbers 50–67 and 451–468, respectively, of the flagellin gene sequence (12).

A probe sequence was chosen which was complementary to the DNA encoding the portion of the flagellin gene sequence and which was not complementary to the primer sequences. The probe chosen was complementary to nucleotide numbers 300–319 of the flagellin gene sequence (12). This probe is labeled so that it can be detected after hybridization of the probe to its complementary DNA sequence. Any suitable labelling method known to those skilled in the art can be used, such as radiolabeled molecules, fluorescent molecules, enzymes, or ligands. In one embodiment, biotin was used as the label in order to provide a nonradioisotopic detection method.

It will be readily apparent to those skilled in the art that although specific sequences are disclosed herein for the primers and probes of the subject invention (see Materials and Methods section), variations in the specific sequences would result in probes and primers which are within the scope of the subject invention. Any primer or probe which is complementary to a portion of the flagellin gene of *Borrelia* which is conserved among species, so as to permit genus-specific probes and primers, can be utilized in the subject invention. This includes, therefore, sequences altered in one or more base pairs from the sequences disclosed and claimed herein, as long as the resulting sequences are similar in function (the function being to encode a portion of the flagellin gene). Thus, sequences having substantially the same nucleotide sequence can also be used as primers and probes in this invention.

After the selection of suitable primers and probes, the primers and probes can be used to detect the presence of *Borrelia* in a sample. The sample is treated to as to lyse any *Borrelia* cells present therein. This can be accomplished using any suitable lysing agent. The lysis of the cells allows the primers and probes to be able to contact the DNA of the *Borrelia* cells. Any other suitable method known to those skilled in the art can be used to "free" the DNA from within the cells for contact with the primers and probes.

The resulting lysed cells are contacted with the labeled probe oligomer, if amplification is not desired, or contacted with the primers if PCR amplification is desired. The PCR amplification allows detection of minute amounts of the *Borrelia* DNA originally present in the sample. Using the specific primers of the subject invention, the sequence of the amplification product is complementary to nucleotide numbers 50–486 of the flagellin gene sequence (12). After the *Borrelia* DNA is amplified, the amplified DNA is then detected, either by contacting with the labeled probe oligomer, which is complementary to the amplified sequence, or by other means known to those skilled in the art, such as agarose gel electrophoresis.

Those skilled in the art will readily recognize this as a PCR assay. As such, any modifications and revisions to the method known to those skilled in the art are equally applicable to the subject invention.

The subject invention is best utilized in a commercial setting by providing the desired DNA oligomers, primers and/or probes, in the form of a kit. The kit may comprise suitable amounts of the primers, or a suitable amount of the probe, or suitable amounts of the primer and probe, in addition to containing suitable amounts of a standard sample (or series of standard samples of varying known concentrations of *Borrelia*), and a control sample substantially free of *Borrelia*. A kit containing only primer sequences can be used to amplify DNA present in a test sample. The amplification products are then detected using suitable means, e.g. by agarose gel electrophoresis. Other means for detecting the amplification product known to those skilled in the art could also be utilized.

If a probe is also supplied with the primer sequences, the amplified product is detected using the probe as discussed previously.

A kit may also be provided which contains only the probe sequence, in which case the complementary sequence of the flagellin gene is detected using the probe without being amplified using PCR. These kits provide for qualitative and/or quantitative detection of *Borrelia* in a test sample. Using the probe and/or primers of the subject invention, minute amounts of *Borrelia* can be detected in the test sample. Furthermore, both European and American strains of *Borrelia burgdorferi* and other species of *Borrelia* can be detected due to the genus-specificity of the subject invention. This is due to conservation of the portion of the flagellin gene which is complementary to the probe used in the subject invention.

Materials and Methods

Spirochetes and cultivation

Two strains of *B. burgdorferi*, the American prototype strain (ATCC-35210) and an isolate from Switzerland (ATCC-35211) were obtained from the American Type Culture Collection (ATCC). Also obtained were cultures of *B. hermsii* (ATCC-35209) and *Treponema pallidum* (ATCC-27087). Cultures of *B. anserina, B. coriaceae, B. hermsii, B. parkeri,* and *B. turicatae* were provided by Dr. Thomas Schwan, Laboratory of Pathobiology, Rocky Mountain Laboratories, National Institute of Allergy and Infectious Diseases, Hamilton, Mont. The *B. burgdorferi* strains were maintained in BSK II medium and passaged weekly (2). The culture of *T. pallidum* was reconstituted in 0.5ml of BSK II medium and used immediately. Other cultures were used as received.

Primer and probe sequences

The target for PCR amplification was the *B. burgdorferi* flagellin gene (12). Two primers, both 18-mers, were selected from a portion of the gene conserved in both American and European strains of *B. burgdorferi*. These primers, designated 1F and 2F (SEQ ID NO: 1 and SEQ ID NO:2, respectively), flanked a 383 bp region of the flagellin gene resulting in a 419 bp PCR amplification product. Primer sequences were as follows: 1F-5′GCATTAACGCTGCTAATC (SEQ ID NO: 1) and 2F-5′TTGCAGGCTGCATTCCAA (SEQ ID NO: 2). Also selected from the flagellin gene sequence was a 20-mer probe for detection of the amplified product by hybridization. The probe was selected such that it did not hybridize with either of the primer sequences and both ends were biotinylated: 5′CACATATTCAGATGCAGACA (SEQ ID NO: 3). The oligonucleotide primers and probe were synthesized by Genesys Biotechnologies, Inc., Woodlands, Tex. and can be synthesized using any known DNA synthesizers (e.g. the Milligen 7500, Millipore Corp., Milford, Mass.).

PCR amplifications for sensitivity and specificity

Enumeration of *B. burgdorferi* was routinely performed using the method of Stoenner (34). For sensitivity studies, appropriate amounts of culture were aliquoted out such that 0.5 ml tubes (Sarsted, Newton, NC) theoretically contained 10,000, 1,000, 100, 10, and 1 cell and volumes were adjusted to 10 μl with 0.9% NaCl. For the specificity analysis, 2 μl of culture was placed into tubes with 3 μl of 0.9% NaCl. An equal volume of the detergent NP-40 (Sigma Chemical Co., St. Louis, Mo.) was added to the cells. The tubes were then placed in a boiling water bath for 5 minutes and were cooled rapidly on ice. PCR reagents were added directly to the entire contents of the tubes. A negative control was prepared using BSK II medium and treated as sample tubes. A positive control was prepared using 20 ng of purified *B. burgdorferi* DNA as a template. The PCR reagent mixture contained: 10mM Tris hydrochloride, 50 mM MgClz, 0.01% gelatin, 200 μM each deoxynucleotide triphosphates, and 1 M of each primer, 1F and 2F (SEQ ID NO: 1 and SEQ ID NO: 2, respectively). All reactions were performed in a Coy TempCycler Model 50 (Ann Arbor, Mich.). The temperature profile used was: template denatured at 94° C. for 2 minutes, primers annealed at 55° C. for 2 minutes, and extension at 72° C. for 3 minutes, for a total of 30 cycles. The amplification products were analyzed in 2% agarose by submarine gel electrophoresis and a standard TAE buffer (19). Ethidium bromide (1 μg/ml) was included in the electrophoresis buffer and gel, and bands were visualized by UV transillumination.

Hybridization

Five microliter aliquots of the PCR amplification products were heat-denatured and directly spotted onto a nitrocellulose membrane (Bethesda Research Laboratories, Gaithersburg, Md.) which had been wetted in 2X distilled autoclaved water and briefly soaked in 10X SSC, then blotted between two sheets of Whatman Chromatography paper #1. The membrane was then baked at 80° C. for 1.5 hours, prehybridized for 30 minutes in a solution of 5X SSC, 5X Dehardt's solution, 5mM EDTA, 0.2% SDS, 0.05% sodium pyrophosphate, and 50 μg/ml *E. coli* tRNA (Sigma Chemical Co., St. Louis, Mo.). Probe (SEQ ID NO: 3) was diluted in the prehybridization solution to 25 μg/ml and was used as the hybridization solution. Hybridization was allowed to take place overnight at 42° C. The membrane was washed three times in 0.16X SSC, 0.1% SDS; twice for 5 minutes at room temperature, the third for 30 minutes at 42° C. The membrane was then rinsed once in 1X SSC for 3 minutes at room temperature and once in 0.1M Tris (pH 7.5), 0.15M NaCl for three minutes at room temperature. Hybrids were detected using the BluGENE Nonradioactive Nucleic Acid Detection System (Bethesda Research Laboratories, Gaithersburg, Md.). The only modification from the protocol suggested by the manufacturer was that the 3% BSA wash was performed for 1.5 hours at 42° C. rather than 1 hour at 65° C.

RESULTS

Sensitivity study

Figure 1:
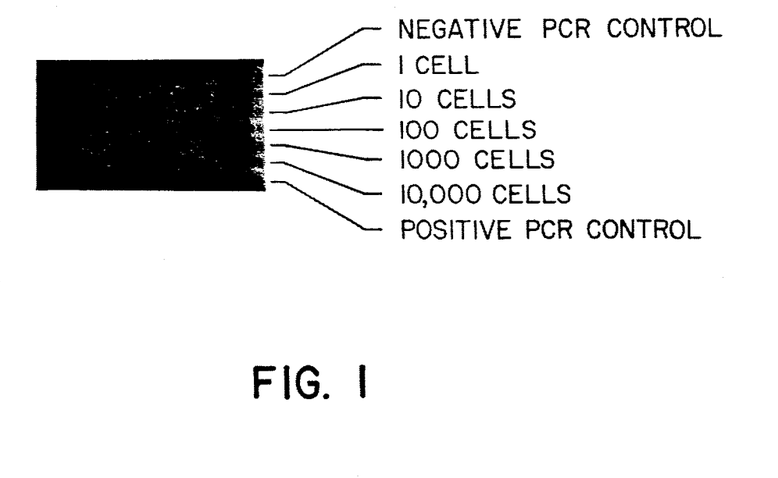
FIG. 1 shows the agarose gel analysis of the sensitivity experiment with *B. burgdorferi* (ATCC-35210) using flagellin primers of the subject invention.
Figure 2:
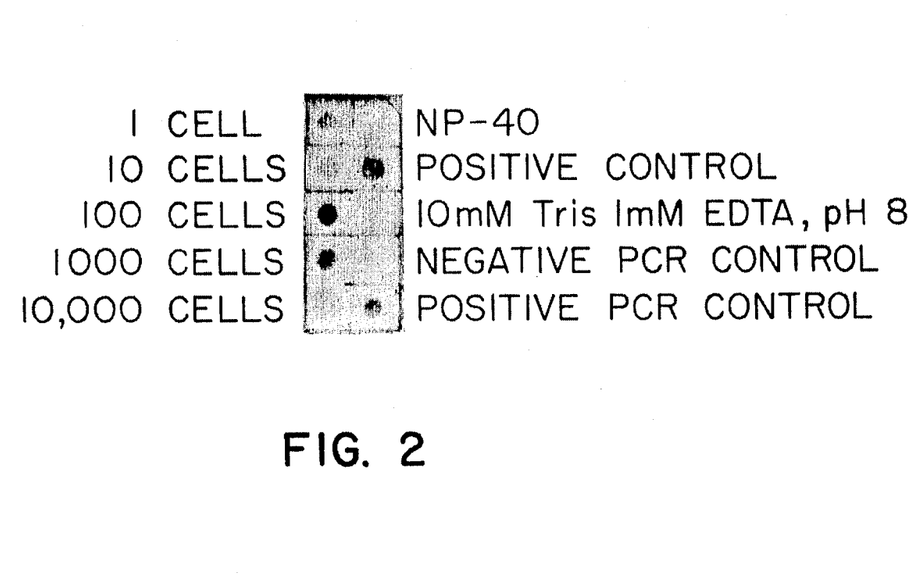
FIG. 2 shows the results of the hybridization analysis of the PCR products from the sensitivity study, by indicating the number of cells detected using PCR and a nonradioisotopic membrane detection system.

FIG. 1 shows the agarose gel analysis of the sensitivity experiment with *B. burgdorferi* (ATCC-35210). The 419 bp PCR amplification product can clearly be seen in lanes 3-6 ranging from 10 to 10,000 cells. A faint band was visible in the one cell lane on the UV transilluminator. No amplification was observed in the negative control lane. The results of the hybridization analysis of the PCR products from the sensitivity study are shown in FIG. 2. No reactivity was noted in the various negative control spots and the one and ten cell spots are clearly visible. These data, coupled with the direct visualization in the agarose gel suggest detection at or near the single cell detection limit.

Specificity study

Figure 3:
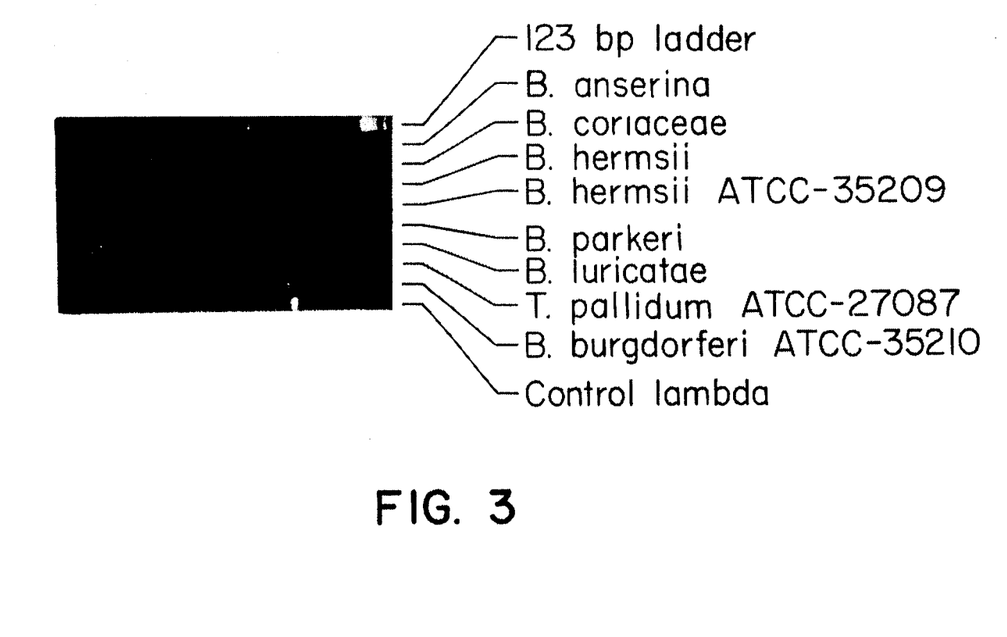
FIG. 3 shows the agarose gel analysis of the specificity analysis using flagellin primers of the subject invention.
Figure 4:
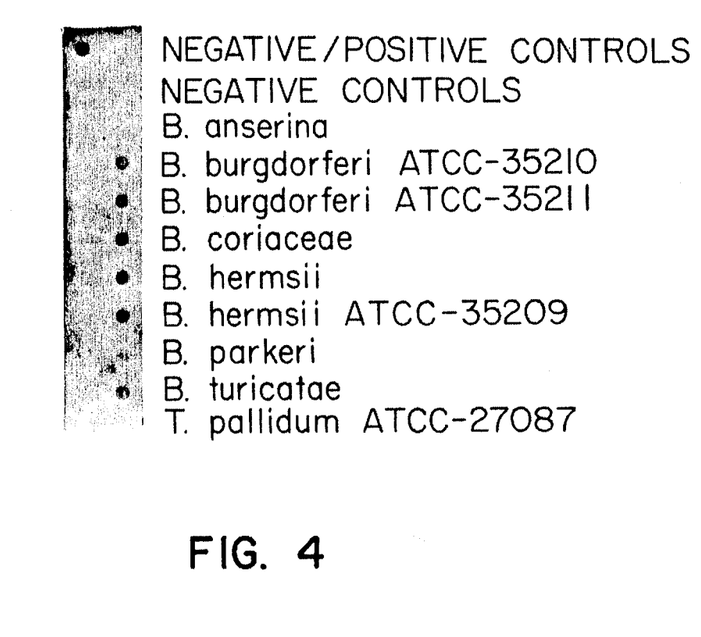
FIG. 4 shows the results of the hybridization analysis of the PCR products from the specificity study, by indicating the number of cells detected using PCR and a nonradioisotopic membrane detection system.

FIGS. 3 and 4 show the agarose gel and hybridization results from the specificity analysis. Reactivity can be seen with all of the *Borrelia* species pathogenic in mammals, although reactivity was quite faint with *B. parkeri*. No reactivity was noted with the avian pathogen *B. anserina*. *T. pallidum*, or any of the negative control spots.

DISCUSSION

In the sensitivity study, the 419 bp amplification product is directly visible in the agarose gel from as few as one to ten spirochetes. The lower limits of detection are made more visible by the use of hybridization, and single cell dilutions are readily detected with the spot blot. These sensitivity levels are comparable to those demonstrated by other PCR-based assays for the detection of *B. burgdorferi* (24, 26). The nonradioisotopic detection method has advantages over the radioisotopic methods in that problems of expense due to a short half-life, storage and disposal associated with radioactively labeled probes are avoided (19). In addition, biotinylated probes have been determined to have sensitivities similar to those reported with radioactively labeled probes. As evidenced by visible bands in the agarose gel and visualization by hybridization, our assay is approaching the single cell detection limit.

In the specificity study, the 419 bp amplification product is directly visible in all of the *Borrelia* species pathogenic in mammals. No amplification product is noted with the avain pathogen *B. anserina* and only faint reactivity is noted with *B. parkeri*. In DNA homology studies, *B. burgdorferi* has a 31-59% homology with other borreliae; it is most closely related to *B. hermsii* with 59% homology and less related to *B. parkeri* with 37% homology (16). Thus, the lower reactivity with *B. parkeri* is consistent with the overall DNA homologies. In a recent study, a monoclonal antibody to a flagellar epitope was seen to bind with all of the *Borrelia* species evaluated in our assay, including *B. anserina* and *B. parkeri* suggesting that the flagellin gene is highly conserved throughout the genus (5). As evidenced by the bands in the agarose gel and the spot blots, our assay also suggests a genus specific nature of the flagellin gene among the *Borrelia* species pathogenic in mammals. No reactivity is noted with *T. pallidum* using our assay. Immunological testing demonstrates that borreliae and treponemes share common antigens and, as a result, patients having antibodies to *T. pallidum* have been seen to yield false positive results in serological tests for *B. burgdorferi* (14, 18). The N-terminal ends of the *T. pallidum* and *B. burgdorferi* flagellin amino acid sequences have been reported as having 80% homology (9). Even with this degree of homology, however, the stringency of our assay allowed discrimination between these two pathogens.

Furthermore, both European and American strains of *B. burgdorferi* are identified in this assay.

Our method is a direct, PCR-based, genus specific method for detecting mammalian pathogenic borreliae. Treatment associated with Lyme disease and other borrelial diseases are similar enough (15) and epidemiologies are different enough (28) that a genus specific detection method may be both versatile and useful. Furthermore, since the flagellin gene is conserved among the various species of *Borrelia*, this method is suitable for the evaluation of both American and European strains of *B. burgdorferi* and therefore useful for the direct detection of the Lyme disease spirochete.

Although certain preferred embodiments have been depicted and described in detail herein, it will be apparent to those skilled in the relevant art that various modifications, additions, substitutions and the like can be made without departing from the spirit of the invention, and these are therefor considered to be within the scope of the invention as defined by the appended claims.

REFERENCES

1. Abbott, M. A. et al., The Journal of Infectious Diseases 158: 1158-1169 (1988).
2. Barbour, A. G., "Isolation and cultivation of Lyme disease spirochetes", in Steere, A. C. et al., eds., Lyme disease: first international symposium, Yale Journal of Biology and Medicine, pp. 71-75 (New Haven, Conn. 1984).
3. Barbour, A. G., Journal of Clinical Microbiology 26: 475-478 (1988).
4. Barbour, A. G. and Garon, C. F., Science 237: 409-411 (1987).
5. Barbour, A. G. et al., Infection and Immunity 52: 549-554 (1986).
6. Barbour, A. G. et al., The Journal of Infectious Diseases 152: 478-484 (1985).
7. Barbour, A. G. et al., Infection and Immunity 45: 94-100 (1984).
8. Burgdorfer, W. et al., Science 216: 1317-1319 (1982).
9. Coleman, J. L. and Benach, J. L., J. Clin. Invest. 84: 322-330 (1989).
10. Dattwyler, R. J. et al., The New England Journal of Medicine 319: 1441-1446 (1988).
11. De, B. K. and Srinivasan, A., Nucleic Acids Research 17: 2142 (1989).
12. Gassmann, G. S. et al., Nucleic Acids Research 17: 3590 (1989).
13. Golightly, M. G. et al., Laboratory Medicine 21: 299-304 (1990).
14. Hansen, K. et al., Journal of Clinical Microbiology 26: 338-346 (1988).
15. Johnson, R. C., Reviews of Infectious Diseases 11(6): S1505-S1510 (1989).
16. Johnson, R. C. et al., "Taxonomy of the Lyme disease spirochetes", in Steere, A. C. et al., eds., Lyme disease: first international symposium, Yale Journal of Biology and Medicine, pp. 79-87 (New Haven, Conn. 1984).
17. LeFebvre, R. B. et al., Journal of Clinical Microbiology 27: 636-639 (1989).
18. Magnarelli, L. A. et al., The Journal of Infectious Diseases 156: 183-188 (1987).
19. Maniatis, T. et al., "Molecular Cloning: a laboratory manual," p. 156 (Cold Spring Harbor Laboratory Press, N.Y. 1982).
20. Melchers, W. J. G. et al., Journal of Clinical Microbiology 27: 1711-1714 (1989).
21. Milch L. J. and Barbour, A. G., The Journal of Infectious Diseases 160: 351-353 (1989).
22. Mullis, K. B. and Faloona, F. A., Methods in Enzymology 155: 335-350 (1987).
23. Mullis, K. et al., Cold Spring Harbor Symposia on Quantitative Biology 51: 263-273 (1986).
24. Nielsen, S. L. et al., Molecular and Cellular Probes 4: 73-79 (1990).
25. Persing, D. H. et al., Journal of Clinical Microbiology 28: 566-572 (1990).
26. Rosa, P. A. and Schwan, T. G., The Journal of Infectious Diseases 160: 1018-1029 (1989).
27. Saiki, R. K. et al., Science 230: 1350-1354 (1985).

28. Schmid, G. P., Reviews of Infectious Diseases 11(6): S1460–S1469 (1989).

34. Stoenner, H. G., Applied Microbiology 28: 540–543 (1974).

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: genomic DNA
        ( A ) DESCRIPTION: primer sequence     ( i i i ) HYPOTHETICAL: no     ( i v ) ANTI-SENSE: no     ( x i ) SEQUENCE DESCRIPTION: SEQ ID NO: 1:

GCATTAACGCTGCTAATC   18

( 2 ) INFORMATION FOR SEQ ID NO: 2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: genomic DNA
        ( A ) DESCRIPTION: primer sequence     ( i i i ) HYPOTHETICAL: no     ( i v ) ANTI-SENSE: no     ( x i ) SEQUENCE DESCRIPTION: SEQ ID NO: 2:

TTGCAGGCTGCATTCCAA   18

( 2 ) INFORMATION FOR SEQ ID NO: 3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: genomic DNA
        ( A ) DESCRIPTION: probe sequence     ( i i i ) HYPOTHETICAL: no     ( i v ) ANTI-SENSE: no     ( x i ) SEQUENCE DESCRIPTION: SEQ ID NO: 3:

CACATATTCAGATGCAGACA   20

29. Schmid, G. P. et al., Journal of Clinical Microbiology 20: 155–158 (1984).

30. Steere, A. C., The New England Journal of Medicine 321: 586–596 (1990).

31. Steere, A. C. et al., The New England Journal of Medicine 312: 869–874 (1985).

32. Steere, A. C. et al., The New England Journal of Medicine 308: 733–740 (1983).

33. Steffan, R. J. and Atlas, R. M., Applied and Environmental Microbiology 54: 2185–2191 (1988).

What is claimed is:

1. A DNA oligomer consisting essentially of a DNA sequence complementary to a portion of a flagellin gene of *Borrelia burgorferi*, the portion being conserved among *Borrelia* species pathogenic in mammals, wherein the DNA sequence is selected from the group consisting of:

SEQ ID NO: 1: 5' GCATTAACGCTGCTAATC,

SEQ ID NO: 2: 5' TTGCAGGCTGCATTCCAA, and

SEQ ID NO: 3: 5' CACATATTCAGATGCAGACA.

2. The DNA oligomer of claim 1 labeled with a detectable marker.

3. The DNA oligomer of claim 2, wherein the detectable marker comprises a marker selected from the group consisting of a radiolabeled molecule, a fluorescent molecule, an enzyme, a ligand, and biotin.

4. The DNA oligomer of claim 3, wherein the detectable marker comprises biotin.

5. A method for detecting in a sample the presence of Borrelia species pathogenic in mammals which comprises:
   (a) treating the sample with a lysing agent so as to lyse any Borrelia cells present in the sample;
   (b) contacting the resulting sample with the labeled DNA oligomer of claim 10 under conditions permitting hybridization of the DNA oligomer to complementary DNA of Borrelia species pathogenic in mammals present in the sample;
   (c) removing unhybridized, labeled DNA oligomer; and
   (d) detecting the presence of any hybrid of the labeled DNA oligomer and complementary DNA of Borrelia species pathogenic mammals in the sample, thereby detecting the presence of Borrelia species pathogenic in mammals in the sample.

6. The method of claim 5, wherein the detectable marker comprises biotin.

7. The method of claim 5, wherein the Borrelia species pathogenic in mammals comprises Borrelia burgdorferi.

8. A method for detecting in a sample the presence of Borrelia species pathogenic in mammals which comprises:
   (a) treating the sample so as to lyse any Borrelia cells present in the sample;
   (b) contacting the resulting sample with a first DNA oligomer consisting essentially of

SEQ ID NO: 1: 5' GCATTAACGCTGCTAATC and with a second DNA oligomer consisting essentially of

SEQ ID NO: : 5' TTCCAGGCTGCATTCCAA under conditions suitable for hybridization of the first and second oligomers to complementary DNA of Borrelia species pathogenic in mammals present in the sample and enzymatic amplification of DNA of the Borrelia species pathogenic in mammals located between the hybridization sites of the first and second DNA oligomers, so as to amplify the DNA of the Borrelia species pathogenic in mammals located between the hybridization sites; and
   (c) detecting the amplified DNA of the Borrelia species pathogenic in mammals, thereby detecting the presence of Borrelia species pathogenic in mammals in the sample.

9. The method of claim 8, wherein the detection in step (c) comprises:
   (a) contacting the resulting sample containing the amplified DNA of the Borrelia species pathogenic in mammals with a labeled third DNA oligomer consisting essentially of SEQ ID NO: 3: 5' CACATATTCAGATGCAGACA
   under conditions permitting hybridization of the third DNA oligomer to the amplified DNA of the Borrelia species pathogenic in mammals present in the sample;
   (b) removing any unhybridized, labeled third DNA oligomer; and
   (c) detecting the present of any hybrid of the labeled third DNA oligomer and the amplified DNA of the Borrelia species pathogenic in mammals, thereby detecting the presence of Borrelia species pathogenic in mammals in the sample.

10. The method of claim 9, wherein the label of the third DNA oligomer comprises biotin.

11. The method of claim 10, wherein the detection in step (c) comprises detecting the biotin label.

12. The method of claim 8, wherein the detection in step (c) comprises subjecting the amplified DNA of the Borrelia species pathogenic in mammals to agarose gel electrophoresis.

13. The method of claim 8, wherein the treating in step (a) comprises treating the sample with a lysing agent.

14. The method of claim 8, wherein the sample comprises urine.

15. The method of claim 8, wherein the sample comprises blood.

16. The method of claim 8, wherein the Borrelia species pathogenic in mammals comprises Borrelia burgdorferi.

* * * * *

UNITED STATES PATENT AND TRADEMARK OFFICE
CERTIFICATE OF CORRECTION

PATENT NO. :  5,283,175
DATED      :  February 1, 1994
INVENTOR(S) : Weaver et al.

It is certified that error appears in the above-indentified patent and that said Letters Patent is hereby corrected as shown below:

In column 10, line 62, claim 1, change "burgorferi" to -- burgdorferi --.

In column 11, line 20, claim 5, change "of claim 10" to
-- of claim 2 --.

In column 11, line 29, claim 5, after "pathogenic" insert -- in --.

In column 11, line 50, claim 8, change

"SEQ ID NO:: 5' TTCCAGGCTGCATTCCAA" to

--SEQ ID NO: 2: 5' TTCCAGGCTGCATTCCAA--.

In column 12, line 28, claim 9, change "present" to -- presence --.

Signed and Sealed this

Twelfth Day of July, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,283,175
DATED : February 1, 1994
INVENTOR(S) : Terry L. Weaver, et al.

It is certified that error appears in the above-indentified patent and that said Letters Patent is hereby corrected as shown below:

In column 10, line 62, claim 1, change "burgorferi" to --burgdorferi--.

In column 11, line 20, claim 5, change "of claim 10" to --of claim 2--.

In column 11, line 29, claim 5, after "pathogenic" insert --in--.

In column 11, line 50, claim 8, change

"SEQ ID NO: 5' TTCCAGGCTGCATTCCAA" to

--SEQ ID NO: 2: 5' TTGCAGGCTGCATTCCAA--.

In column 12, line 28, claim 9, change "present" to --presence--.

This certificate supersedes Certificate of Correction issued July 12, 1994.

Signed and Sealed this

Fifteenth Day of November, 1994

Attest:

BRUCE LEHMAN

*Attesting Officer*     *Commissioner of Patents and Trademarks*